(12) United States Patent
Li

(10) Patent No.: US 7,831,081 B2
(45) Date of Patent: Nov. 9, 2010

(54) BORDER DETECTION IN MEDICAL IMAGE ANALYSIS

(75) Inventor: Wenguang Li, Campbell, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 658 days.

(21) Appl. No.: 11/409,343

(22) Filed: Apr. 20, 2006

(65) Prior Publication Data

US 2007/0036404 A1 Feb. 15, 2007

Related U.S. Application Data

(60) Provisional application No. 60/708,479, filed on Aug. 15, 2005.

(51) Int. Cl.
*G06K 9/00* (2006.01)
*A61B 8/00* (2006.01)
*G06K 9/48* (2006.01)

(52) U.S. Cl. .................. 382/131; 600/437; 600/443; 382/128; 382/199; 128/922

(58) Field of Classification Search .......... 600/407–472
See application file for complete search history.

(56) References Cited

U.S. PATENT DOCUMENTS

| | | | |
|---|---|---|---|
| 4,907,156 A | 3/1990 | Doi et al. |
| 5,107,838 A | 4/1992 | Yamaguchi |
| 5,301,286 A | 4/1994 | Rajani |
| 5,360,006 A | 11/1994 | Geiser et al. |
| 5,520,185 A | 5/1996 | Soni et al. |
| 5,655,535 A | 8/1997 | Friemel et al. |
| 5,734,739 A | 3/1998 | Sheehan et al. |
| 5,797,396 A | 8/1998 | Geiser et al. |
| 5,855,218 A | 1/1999 | Giannetti |
| 5,928,151 A | 7/1999 | Hossack et al. |
| 6,048,314 A | 4/2000 | Nikom |
| 6,106,465 A | 8/2000 | Napolitano |

(Continued)

FOREIGN PATENT DOCUMENTS

EP 1 076 318 2/2001

(Continued)

OTHER PUBLICATIONS

Wenguang Li, "Image and Signal Processing in Intravascular Ultrasound," printed by Ridderprint B.V., Ridderkirk, Jun. 27, 1997.

(Continued)

*Primary Examiner*—Long V Le
*Assistant Examiner*—Angela M Hoffa
(74) *Attorney, Agent, or Firm*—Frommer Lawrence & Haug LLP; Patrick R. Turner

(57) ABSTRACT

A system and method of analysis for a medical image are described. A medical image is received and analyzed, and an initial border of a region within the medical image is determined based on the analysis of the medical image. A user input is received indicating one or more control points, where each of the one or more control points is located inside or outside of the initial border. A modified border of the region is determined based on the analysis and the user input, the modified border passing through the one or more control points.

32 Claims, 7 Drawing Sheets

U.S. PATENT DOCUMENTS

| | | |
|---|---|---|
| 6,106,466 A | 8/2000 | Sheehan et al. |
| 6,120,445 A | 9/2000 | Grunwald |
| 6,132,373 A | 10/2000 | Ito et al. |
| 6,165,128 A | 12/2000 | Céspedes et al. |
| 6,181,810 B1 | 1/2001 | Zhang et al. |
| 6,264,609 B1 | 7/2001 | Herrington et al. |
| 6,287,259 B1 | 9/2001 | Grunwald |
| 6,301,498 B1 | 10/2001 | Greenberg et al. |
| 6,346,124 B1 | 2/2002 | Geiser et al. |
| 6,381,350 B1 | 4/2002 | Klingensmith et al. |
| 6,385,332 B1 | 5/2002 | Zahalka et al. |
| 6,544,179 B1 | 4/2003 | Schmiesing et al. |
| 6,705,994 B2 | 3/2004 | Vortman et al. |
| 6,708,055 B2 | 3/2004 | Geiser et al. |
| 6,817,982 B2 | 11/2004 | Fritz et al. |
| 6,835,177 B2 | 12/2004 | Fritz et al. |
| 6,954,938 B2 | 10/2005 | Emberty et al. |
| 2002/0072670 A1* | 6/2002 | Chenal et al. .............. 600/449 |
| 2002/0072671 A1* | 6/2002 | Chenal et al. .............. 600/450 |
| 2004/0037455 A1* | 2/2004 | Klingensmith et al. ...... 382/128 |
| 2004/0122326 A1 | 6/2004 | Nair et al. |
| 2004/0197015 A1* | 10/2004 | Fan et al. ................... 382/128 |
| 2005/0075567 A1 | 4/2005 | Skyba et al. |
| 2005/0249391 A1 | 11/2005 | Kimmel et al. |

FOREIGN PATENT DOCUMENTS

| | | |
|---|---|---|
| WO | WO 98/39736 | 9/1998 |
| WO | 2004/017823 | 3/2004 |
| WO | WO 2004/111937 | 12/2004 |
| WO | WO 2006/016317 | 2/2006 |

OTHER PUBLICATIONS

Gustavsson, T., "Implementation and comparison of four different boundary detection algorithms for quantitative ultrasonic measurements of the human carotid artery," Computers in Cardiology 1997 Lund, Sweden, Sep. 7-10, 1997, New York, NY, USA, IEEE, US, Sep. 7, 1997, pp. 69-72, XP010264457, ISBN: 0-7803-4445-6, abstract, Section 7.1, p. 71.

International Search Report and Written Opinion of the International Searching Authority, PCT Application Serial No. PCT/US2006/031739, Jan. 30, 2007, 12 pp.

Examination Report dated Mar. 4, 2008 from European Application No. 06 801 481.0-2319, 4 pages.

Clemens von Birgelen, M.D., et al., "Morphometric analysis in three-dimensional intracoronary ultrasound: An in vitro and in vivo study performed with a novel system for the contour detection of lumen and plaque," American Heart Journal, vol. 132, No. 3, Sep. 1996, pp. 516-527.

Stein Inge Rabben, et al., "Semiautomatic contour detection in ultrasound M-mode images," Ultrasound In Med. & Biol., vol. 26, No. 2, Feb. 2000, pp. 287-296.

* cited by examiner

BORDER DETECTION IN MEDICAL IMAGE ANALYSIS

CROSS-REFERENCE TO RELATED APPLICATION

This application claims priority to pending U.S. Provisional Application Ser. No. 60/708,479, entitled "Medical Image Analysis", filed on Aug. 15, 2005, the entire contents of which are hereby incorporated by reference.

BACKGROUND

The present invention relates to medical imaging.

Intravascular ultrasound (IVUS) imaging provides medical professionals with real-time, cross-sectional, high-resolution images of the arterial lumen and vessel wall. IVUS imaging permits visualization of lesion morphology and accurate measurements of arterial cross-sectional dimensions in patients. This has led to many important clinical applications including quantitative assessment of the severity of restenosis or the progression of atherosclerosis, the selection and guidance of catheter-based therapeutic procedures, and evaluation of the outcome of intravascular intervention. For example, to assess the level of plaque build-up within an artery, the lumen's border and the artery's border can be detected. The level of plaque is typically the difference between the two borders.

A conventional technique for generating a cross-sectional intravascular ultrasound (IVUS) image of a vessel involves sweeping an ultrasound beam sequentially in a 360-degree scan angle. A single element transducer at the end of a catheter can be rotated inside the vessel. Either the single element transducer can be attached to a flexible drive shaft or a rotating mirror can be used; in either case, the ultrasound beam is directed to substantially all angular positions within the vessel. Alternatively, a large number of small transducer elements can be mounted cylindrically at the circumference of the catheter tip, and the ultrasound beam steered electronically to form a cross-sectional scan.

The interaction of the ultrasound beam with tissue or blood yields an echo signal that is detected by the transducer. Based upon the biological medium that the echo signal interacts with, the echo signal can experience attenuation, reflection/refraction, and/or scattering. When an ultrasound wave travels across the boundary between two types of media, part of the wave is reflected at the interface, while the rest of the wave propagates through the second medium. The ratio between the reflected sound intensity and the intensity that continues through to the second medium is related to the difference in acoustic impedance between the mediums. An IVUS system includes conversion circuitry to convert the echo signals described above into electronic signals capable of being displayed as an ultrasound image, e.g., in a standard video format.

SUMMARY

In general, in one aspect, the invention features a method of analysis for an intravascular ultrasound (IVUS) image. An IVUS image is received and analyzed, and an initial border of a region within the IVUS image is determined based on the analysis of the IVUS image. A user input is received indicating one or more control points, where each of the one or more control points is located inside or outside of the initial border. A modified border of the region is determined based on the analysis and the user input, the modified border passing through the one or more control points.

The details of one or more embodiments of the invention are set forth in the accompanying drawings and the description below. Other features and advantages of the invention will become apparent from the description, the drawings, and the claims.

BRIEF DESCRIPTION OF THE DRAWINGS

Like reference numbers and designations in the various drawings indicate like elements.

DETAILED DESCRIPTION

A method of analysis of an IVUS image is described. An IVUS image is analyzed and an initial border of a region within the IVUS image is determined, e.g., the initial border of the lumen or the initial border of the vessel itself, i.e., the medial-adventitial border. The initial border is displayed to a user superimposed on the IVUS image. The user may elect to modify the initial border by selecting one or more control points either outside or inside of the border. A modified border is determined based on the analysis of the IVUS image and the user selected control points. The modified border passes through the one or more selected control points.

Figure 1:
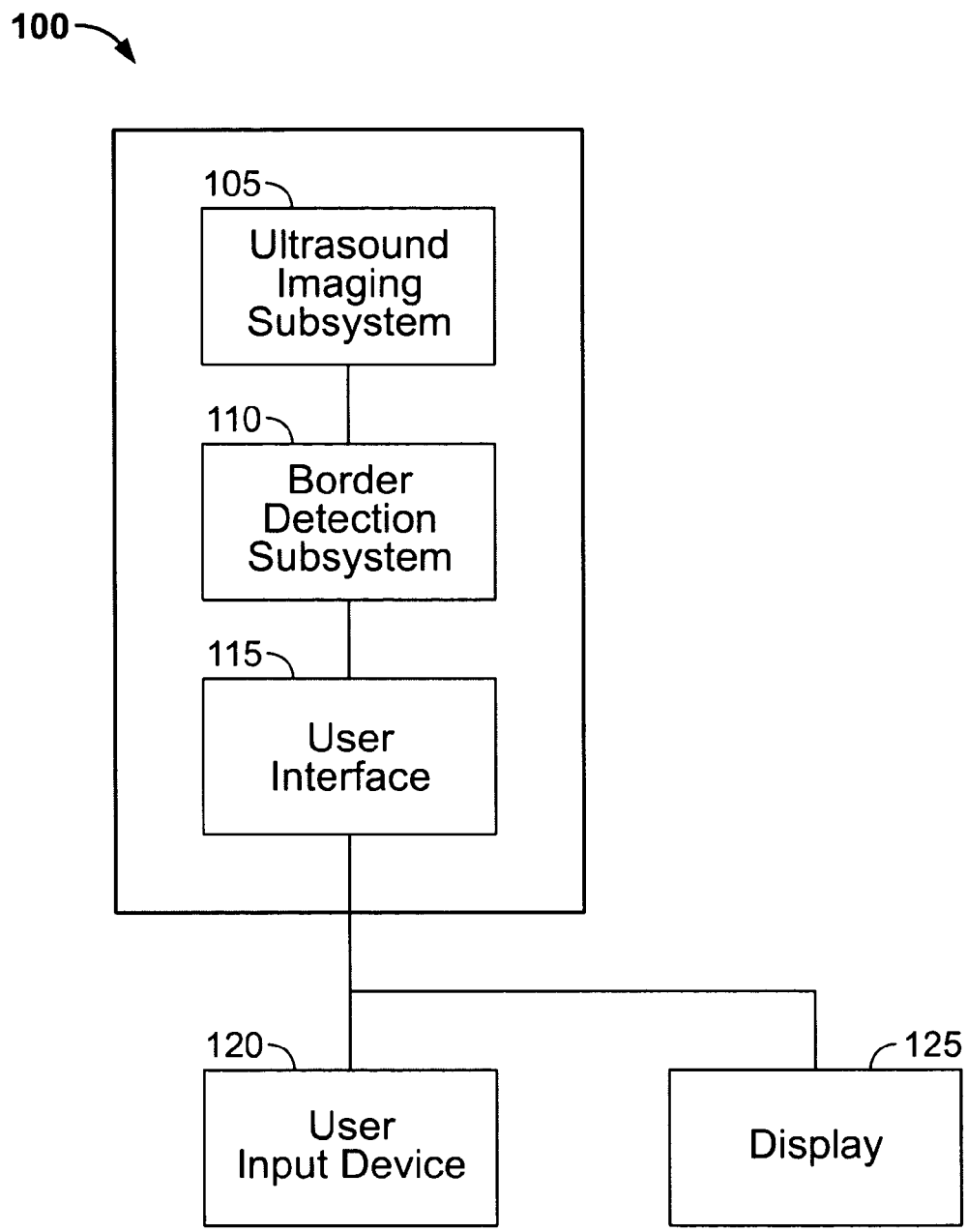
FIG. 1 shows an exemplary system including a border detection subsystem.

FIG. 1 shows one embodiment of a system 100 for receiving and analyzing IVUS images. The ultrasound imaging subsystem 105 included in the system 100 can include an ultrasound transducer, along with software and hardware components that generate an IVUS image based upon the data received from the ultrasound transducer. The system 100 also includes a border detection subsystem 110 configured to analyze the IVUS image and determine the initial border of a region within the IVUS image. A user interface 115 allows a user to interact with the system 100; the user interface 115 can be connected to a user input device 120 and a display 125. In one implementation, the user input device 120 is a trackball and the display 125 is a monitor. In another implementation, the display 125 can be any other suitable display device to allow the user to view the IVUS image, e.g., a television screen, and the input device 120 can be any other suitable user input device to allow the user to provide input to the system, e.g., a keyboard, a light pen, drawing tablet, or touch-sensitive monitor.

Figure 2:
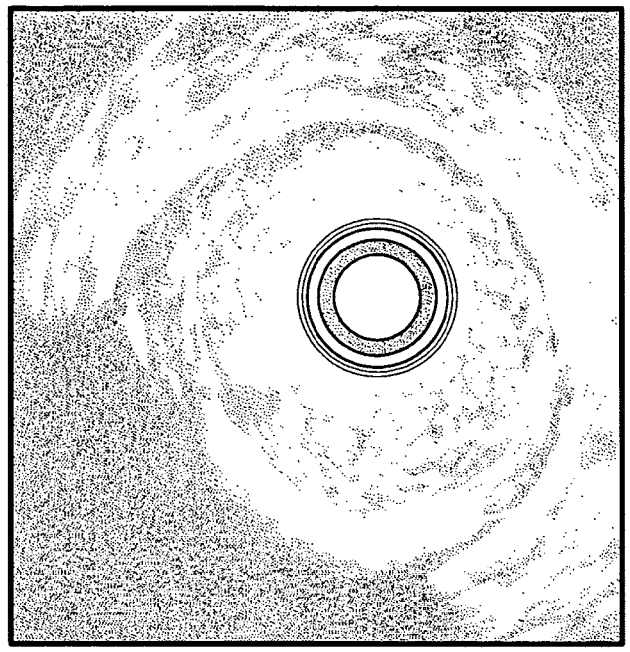
FIG. 2 shows an IVUS image.

FIG. 2 shows an exemplary IVUS image 200 generated by the ultrasound imaging subsystem 105 as displayed on the display 125. To a skilled physician or ultrasound technician, the contrasting areas of the IVUS image 200 provide information about the condition of the blood vessel being imaged.

Figure 3:
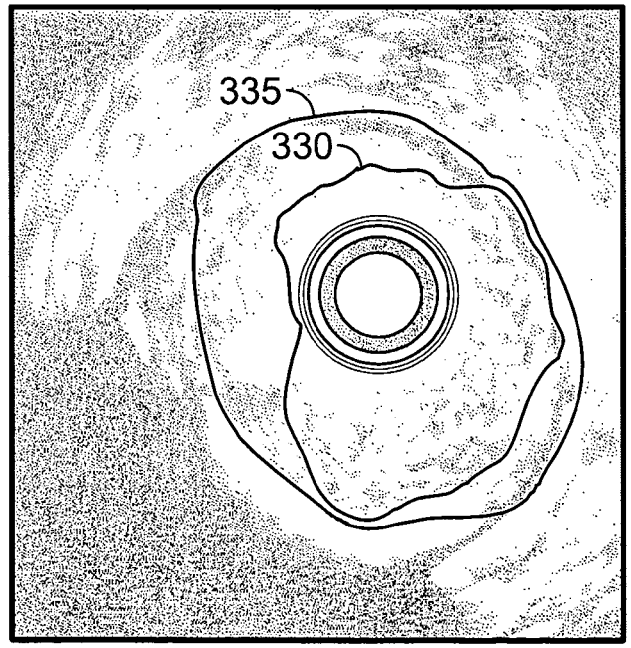
FIG. 3 shows the IVUS image of FIG. 2 with an initial lumen border and medial-adventitial border superimposed on the image.

Referring to FIG. 3, an IVUS image 200 to which one or more edge detection functions have been applied to detect an initial lumen border 330 and an initial medial-adventitial border 335 is shown. Any edge detection technique can be applied, including one or more of the exemplary edge detection techniques described below, or others.

Figure 4:
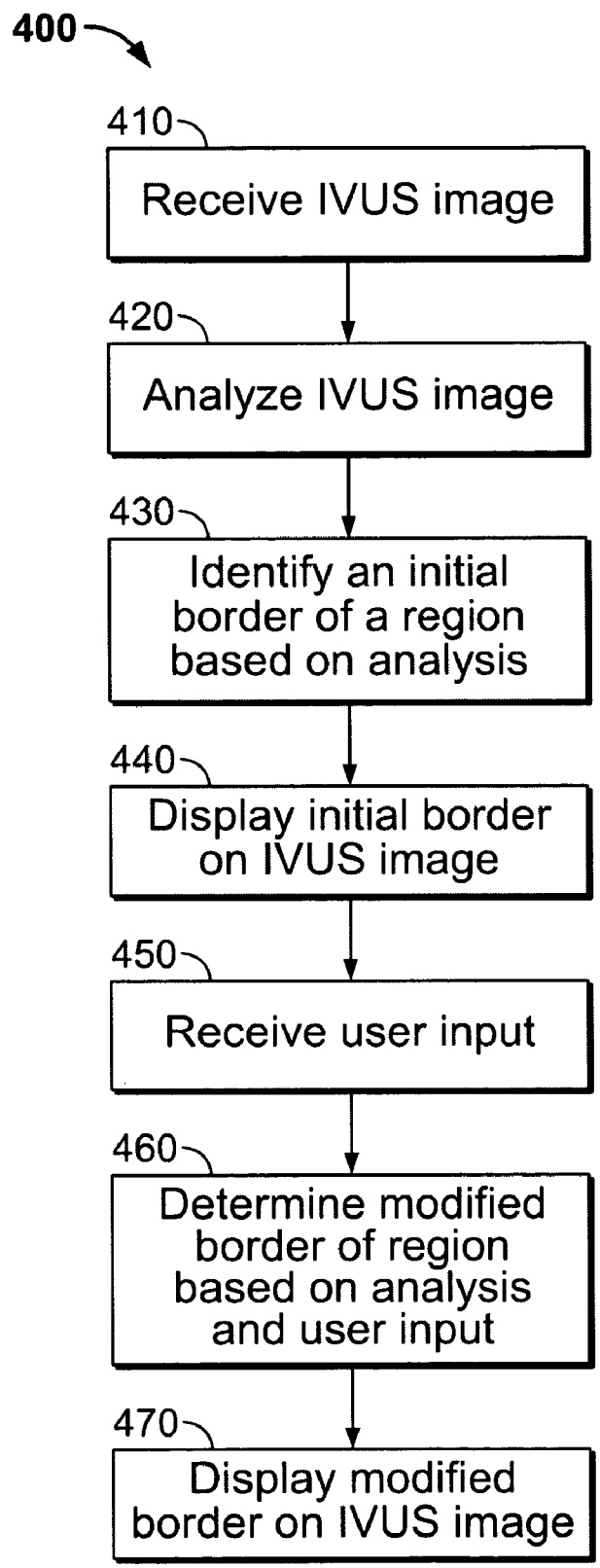
FIG. 4 is a flowchart illustrating a process for analyzing an IVUS image.

FIG. 4 is a flowchart showing a process for calculating an initial border of a region within the IVUS image, such as the medial-adventitial border or the luminal border, and modifying the border based on user input. For illustrative purposes, the process 400 shall be described in reference to the system 100 shown in FIG. 1, however, it should be understood that a different system can be used to perform the process. The border detection subsystem 110 receives an IVUS image, for example, IVUS image 200 shown in FIG. 2 (step 410). In the system 100 shown, the border detection subsystem 110 receives the IVUS image from the ultrasound imaging subsystem 105. In one implementation, the ultrasound imaging subsystem 105 can include an imaging catheter, such as imaging catheters available from Boston Scientific Scimed, Inc., doing business in Fremont, Calif.

Next, the system 100 analyzes the IVUS image (step 420). For example, in one implementation, this includes analyzing the grayscale contrast between pixels. That is, comparing the brightness of pixels and determining regions of contrast. A border typically lies in a region of contrast between pixels having a high brightness versus pixels having a low brightness. The border detection system 110 identifies an initial border of a region based on the analysis (step 430). The initial border can be detected using an edge detection process, including one of the edge detection processes described below, or any other convenient edge detection process.

One example of an edge detection process is the parallel edge detection process. The parallel edge detection process determines whether or not a particular pixel is located on the boundary of the region based upon information within the locality of the pixel only. As this process is local, and is not affected by the processing results in other locations, parallel edge detection techniques may be applied simultaneously everywhere within the IVUS image to find the complete border of the region. A typical parallel edge detection process involves applying an edge operator to enhance the image boundary, finding edge pixels of the enhanced image data by identifying pixels that fall within a given range of values, removing multiple edge points by a thinning algorithm, and linking the edge points to form a contour that encompasses all pixels included in the region, thereby establishing the border of the region.

Another example of an edge detection process is the sequential edge detection process. Sequential edge detection is based on the principle that the border of a physical object (i.e., the region) should be continuous, and when an edge point is identified, its successor is likely to be found in a nearby neighborhood. Consequently, the sequential approach searches for one edge point at a time, which allows using both local information and the results of the previously examined points for decision-making. One implementation of the sequential approach is a radial search method for the detection of a region with a closed and generally circular shape, such as the arterial lumen. The radial search approach can include finding the region's approximate center to define a set of radii, applying an edge operator, searching for an edge point along the radius originated from the center, and then combining all the radial edge points to form a contour. This approach also has the added advantage of turning a two-dimensional boundary detection problem into a one-dimensional search along a set of straight lines.

In another implementation, the initial border is determined based on sequential edge detection with dynamic programming optimization. Dynamic programming optimization is a technique to select optimal edge pixels from a set of possible edge pixel candidates using as much information as possible. In one implementation, an edge strength map is calculated that includes an edge strength value of each image pixel. The edge strength value of a pixel represents the likelihood that an edge passes through the pixel; the higher the edge strength value for a pixel, the more likely the edge passes through the pixel. For example, the grayscale contrast data of the image can be used to determine edge strength values. That is, a pixel in a high contrast region (i.e., a region including high brightness and low brightness pixels in close proximity), has a higher probability of being an edge pixel. Additional data can also be used. For instance, if the medial-adventitial border is calculated first, then any pixel lying outside of the medial-adventitial border has low likelihood of being on an edge representing the luminal border, as the luminal border is conventionally within the medial-adventitial border: this data can be used when calculating edge strength values for an edge representing the luminal border. Other data can be used to calculate the edge strength values, for example, an expected shape of the border. That is, the medial-adventitial border is generally expected to be substantially circular whereas a luminal border may be more irregular.

In other implementation, a spectral analysis of the received ultrasound signals can be performed, and signal phase, amplitude and power information can be derived from the spectral analysis. The blood flowing within the lumen also creates signals that can reduce the contrast between the lumen and the blood. However, echo signals created in the blood flow generally have a different signal phase then echo signals created by the tissue at the luminal border. A spectral analysis of the echo signals can be used to derive the signal phase information, and therefore help differentiate between blood flow and tissue at the luminal border. This information can also be used to determine the edge strength values included in the edge strength map.

The initial border can be determined by using the edge strength map, with the initial border passing through the set of pixels that results in the highest cumulative edge strength value, while still conforming to rules that define the initial border, e.g., the initial border must be a closed curve.

Once determined, the initial border is displayed superimposed on the IVUS image (step 440). FIG. 3 shows the IVUS image 200 of FIG. 2, with two initial borders 330, 335 superimposed on the image 100. The initial border 330 is the luminal border as identified by the border detection subsystem 110, and the initial border 335 is the medial-adventitial border as identified by the border detection subsystem 110.

Figure 5:
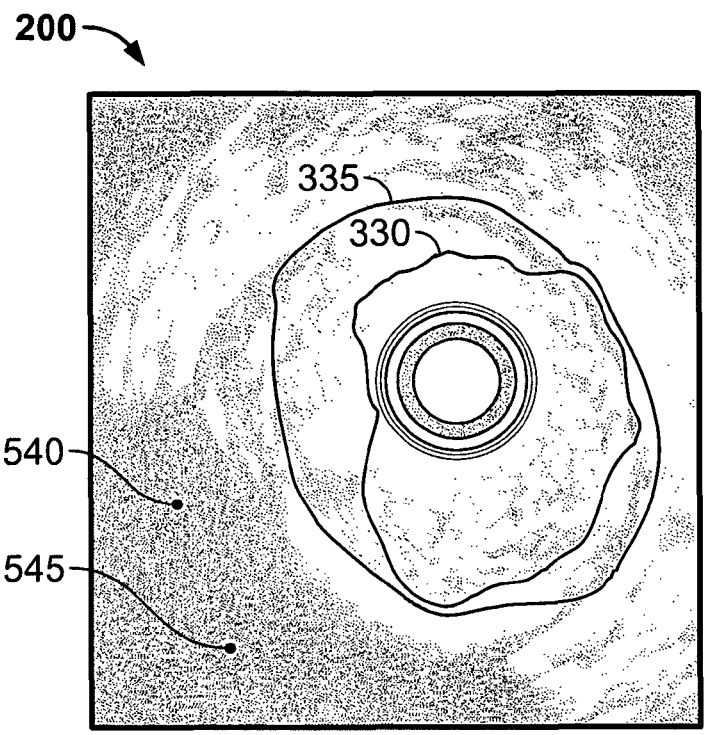
FIG. 5 shows the IVUS image of FIG. 3, with user-selected control points superimposed on the image.

A skilled physician, ultrasound technician, or other trained user of the system can frequently make judgments about the IVUS image that an edge detection function cannot. For example, calcified lesions or plaque within the vessel can obscure the medial-adventitial border and cause the edge detection function to generate a substantially inaccurate representation of a border. In a next step, the border detection subsystem 110 receives user input about modifying one or more of the initial borders (step 450). In one implementation, the user inputs one or more control points using the user input device 120, e.g., by using a trackball to select the control points on the displayed IVUS image 200, with each point displayed for the user. Referring to FIG. 5, the IVUS image 200 is shown with the user-selected points 540, 545 superimposed thereon. In this example, the user wishes to modify the initial medial-adventitial border 335, and wants the modified medial-adventitial border to pass through the points 540, 545.

Figure 6:
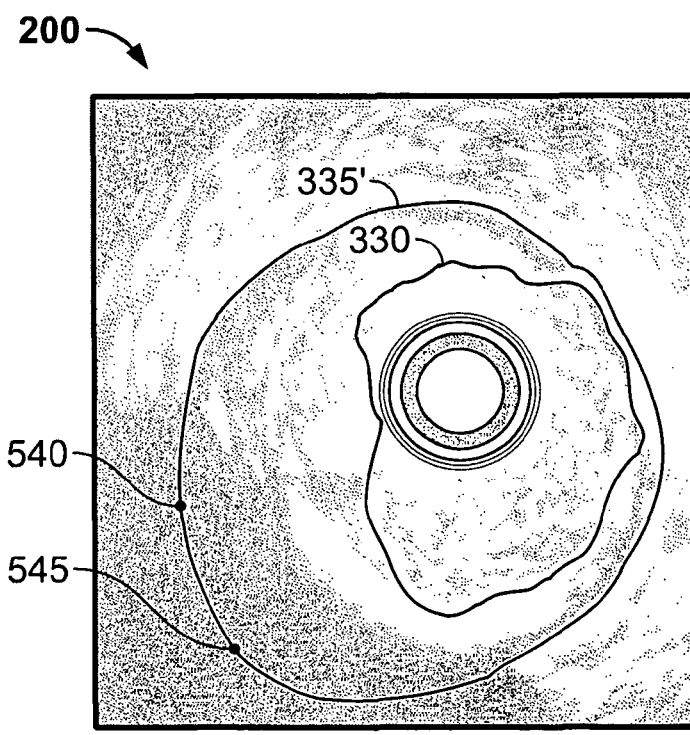
FIG. 6 shows the IVUS image of FIG. 5 with a modified medial-adventitial border superimposed on the image.

The border detection subsystem 110 determines a modified border of the region based on the analysis and the user input, i.e., the control points 540, 545 (step 460). For example, when using the sequential edge detection with dynamic programming optimization technique described above, a selection of a control point can change the edge strength value of one or more corresponding pixels. That is, the one or more pixels representing the control point (or within a predetermined proximity thereto) have a high probability (e.g., 100%) of being on an edge representing the border. The original image analysis is combined with the user input (e.g., selection of control points) to calculate a new or a modified edge strength map. Using the modified edge strength map, the border detection subsystem 110 can determine if the initial border of the region must be modified in order to pass through the control points, and automatically modify the border if necessary. Referring to FIG. 6, the modified border 335' is displayed superimposed on the IVUS image 200 on the display 125 (step 470). As shown, the modified border 335' passes through the control points 540, 545.

Steps 450 through 470 can be repeated as many times as desired, with the user providing one or more additional control points, or replacing one or more existing control points with new control points, during each iteration. In one implementation, if the user selects a new control point located within a predetermined proximity to an existing control point, the new control point replaces the existing control point. In this way, the user can easily adjust the position of the border of the region.

Figure 7:
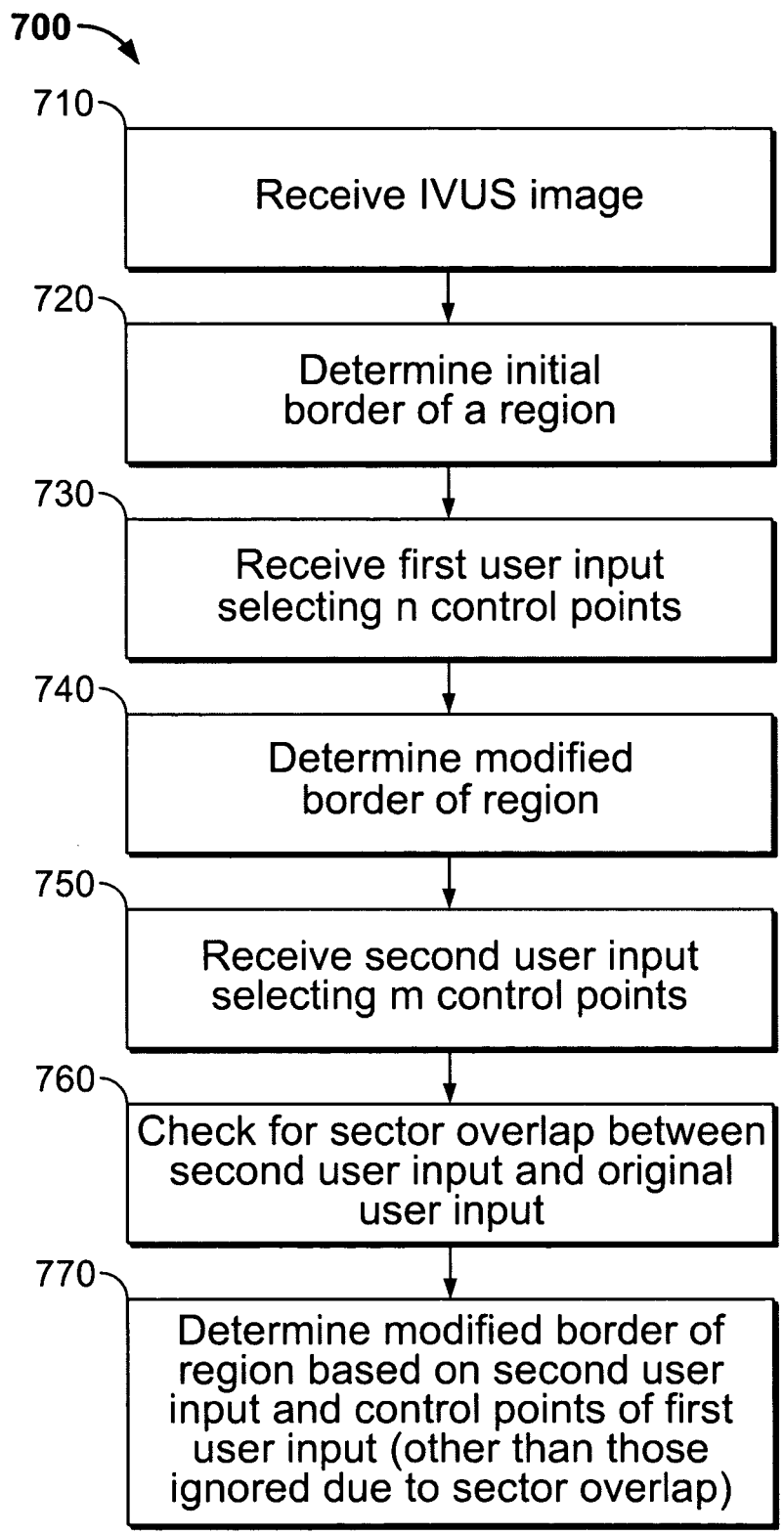
FIG. 7 is a flowchart illustrating a process for analyzing an IVUS image.
Figure 8:
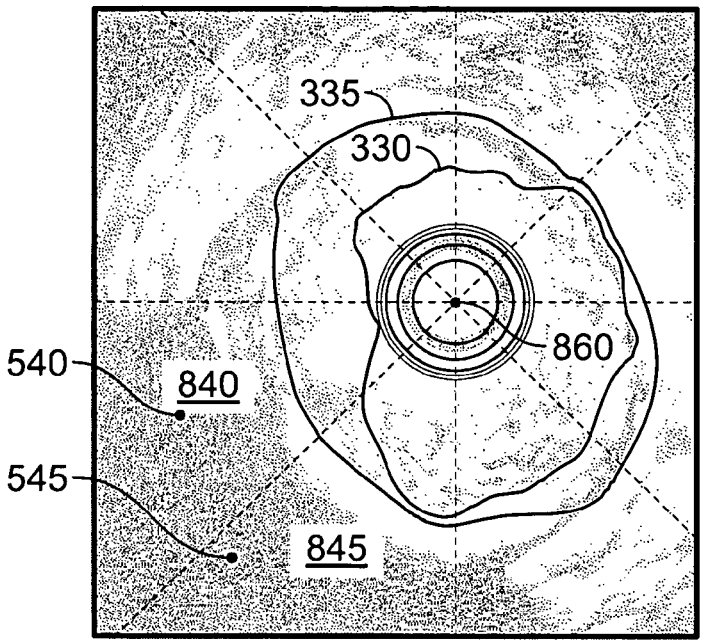
FIG. 8 shows the IVUS image of FIG. 5 with illustrative sector boundaries superimposed on the image.

FIG. 7 shows a method 700 for determining if a new control point is located within a predetermined proximity to an existing control point. The border detection subsystem 110 receives an IVUS image, for example, IVUS image 200 shown in FIG. 8 (step 710). In the system 100 shown, the border detection subsystem 110 receives the IVUS image from the ultrasound imaging subsystem 105. The border detection subsystem 110 divides the image 200 into multiple sectors. FIG. 8 shows one implementation, where the sectors are wedge-shaped and defined by radial lines emanating from an approximate center 860 of the vessel. Although FIG. 8 shows eight wedge-shaped sectors, the IVUS image can be divided into any number of wedge-shaped sectors; e.g., the border detection subsystem 110 can divide the image into 120 to 180 wedge-shaped sectors. Alternatively, the image 200 can be divided into sectors having a different shape.

The border detection subsystem 110 determines an initial border of a region, e.g., the initial medial-adventitial border 335 (step 720), as described above. Next, a first user input selecting n control points is received by the border detection subsystem 110 from the user input device 120 (step 730). In this example, n=2, and the control points are points 540 and 545 shown in FIG. 8.

Figure 9:
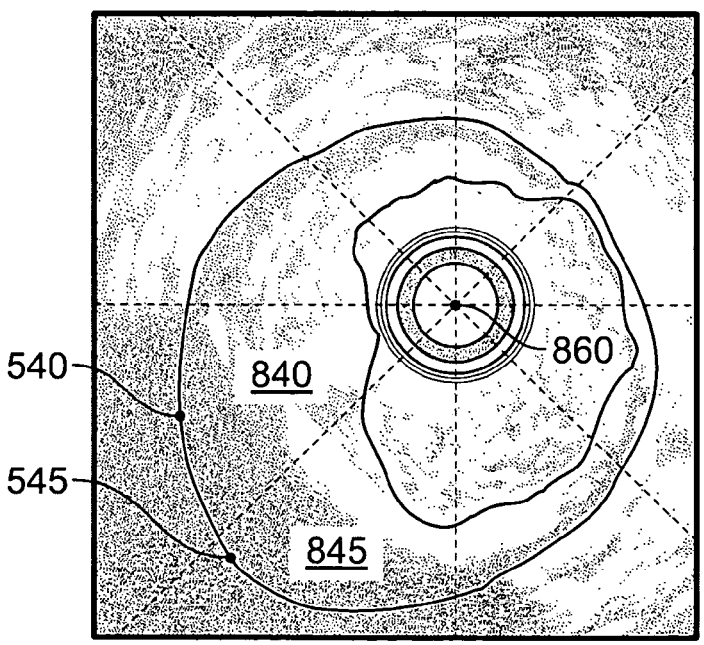
FIG. 9 shows the IVUS image of FIG. 6 with illustrative sector boundaries superimposed on the image.

Referring to FIG. 9, as described above in reference to FIG. 4, the border detection subsystem 110 determines a modified medial-adventitial border 335' of the vessel based on the analysis and the control points included in the first user input (step 740). A second user input selecting m control points is received by the border detection subsystem 110 from the user input device 120 (step 750). In this example, m=2, and points 940 and 945 are the control points received in the second user input, shown in FIG. 10.

Figure 10:
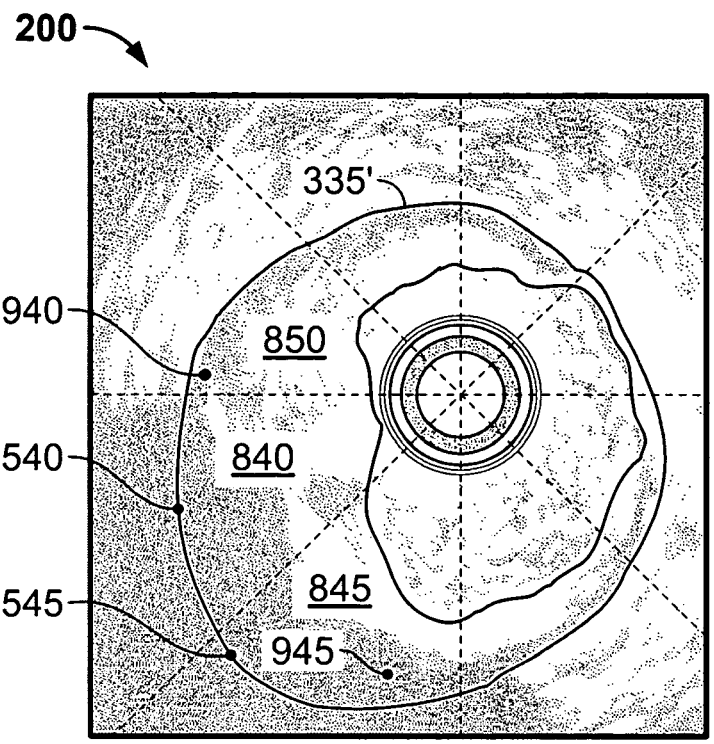
FIG. 10 shows the IVUS image of FIG. 9 with additional control points selected.

The border detection subsystem 110 determines if one or more control points included in the second input are located in the same sector as a control point included in the first input (step 760). If a control point included in the second input is located in the same sector as a control point included in the first input, the control point included in the first input is ignored by the border detection subsystem 110 when determining a further modified border (step 770). As an example, FIG. 10 shows points 540 and 545 as the control points within the first user input. Point 540 is located in sector 840, and point 545 is located in sector 845. Points 940 and 945 are the control points within the second user input, with point 940 located in sector 850 and point 945 located in sector 845. In this instance, the border detection subsystem 110 determines that point 945 is in the same sector as point 545, and ignores point 545 when determining the further modified medial-adventitial border 335" shown in FIG. 11. That is, point 545 is replaced by point 945 within sector 845.

Figure 11:
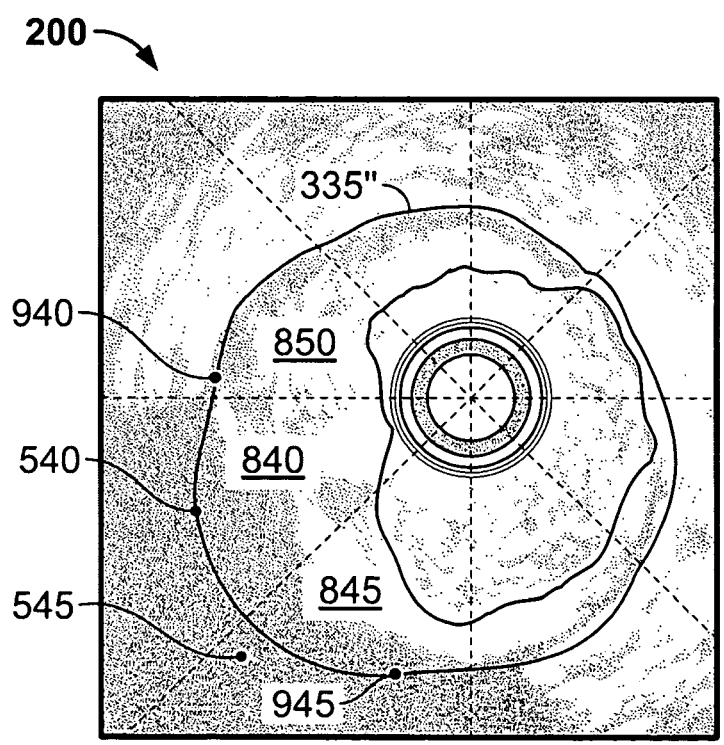
FIG. 11 shows the IVUS image of FIG. 10 with a further modified medial-adventitial border superimposed on the image.

Next, or if no second control point is located in the same sector as a first control point, the border detection subsystem 110 determines a modified border of the region based on the second control points of the second user input, i.e., points 940 and 945 and the remaining first control points of the first user input, if any (step 770), i.e., point 540. If a second control point replaces a first control point, the modified border need only pass through the second control point, as the second control point has replaced the first control point. Referring to FIG. 11, the modified border 335" is displayed superimposed on the IVUS image 200. As shown, the modified border 335" passes through the control points 940, 945 and 540, but does not pass through the replaced control point 545. In one implementation, the replaced control points, e.g., point 545, are not displayed superimposed on the IVUS image 200 by the display 125. The method 700 can be repeated as many times as desired by the user to further modify the border.

In an alternative implementation, the first user input can be received without performing the initial border detection. Alternatively, the initial border can be hidden (i.e., not displayed) while waiting for user input. In either implementation, the user can view the ultrasound image unobstructed by displayed borders, in order to determine where to put the control point or points, as some users may feel that they will be biased if the initial border is displayed. A modified border can then be determined based on the user input, in a similar as was described above.

The techniques described above can also be applied to the field of cardiac ultrasonography (echocardiography) in order to measure the heart chambers. Echocardiography is a non-invasive tool for imaging the heart and surrounding structures, and can be used to evaluate cardiac chamber size and wall thickness. The edge detection techniques discussed above for detecting vessel borders in intravascular ultrasound images can also be applied to echocardiograph images for detecting an initial border of a cardiac chamber, and determining a modified border based at least in part on user input, e.g., the selection of control points indicating definite border points.

A subsystem, as the term is used throughout this application, can be a piece of hardware that encapsulates a function, can be firmware or can be a software application. A subsystem can perform one or more functions, and one piece of hardware, firmware or software can perform the functions of more than one of the subsystems described herein. Similarly, more than one piece of hardware, firmware and/or software can be used to perform the function of a single subsystem described herein.

The invention and all of the functional operations described in this specification can be implemented in digital electronic circuitry, or in computer software, firmware, or hardware, including the structural means disclosed in this specification and structural equivalents thereof, or in combinations of them. The invention can be implemented as one or more computer program products, i.e., one or more computer programs tangibly embodied in an information carrier, e.g., in a machine-readable storage device or in a propagated signal, for execution by, or to control the operation of, data processing apparatus, e.g., a programmable processor, a computer, or multiple processors or computers. A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, subprograms, or portions of code). A computer program can be deployed to be executed on one computer or on multiple computers at one site or distributed across multiple sites and interconnected by a communication network.

The processes and logic flows described in this specification, including the method steps of the invention, can be performed by one or more programmable processors executing one or more computer programs to perform functions of the invention by operating on input data and generating output. The processes and logic flows can also be performed by, and apparatus of the invention can be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, the invention can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The invention has been described in terms of particular embodiments. Other embodiments are within the scope of the following claims. For example, the steps of the invention can be performed in a different order and still achieve desirable results.

What is claimed is:

1. A method of analysis for an intravascular ultrasound (IVUS) image comprising:
   receiving an IVUS image;
   analyzing the IVUS image;
   determining an initial border of a region within the IVUS image based on the analysis of the IVUS image;
   receiving a first user input interacting with a display device to indicate one or more first control points on the IVUS image displayed on the display device, wherein each of the one or more first control points is independent of the initial border and located inside or outside of the initial border;
   determining a first modified border of the region based on the analysis and the first user input, the first modified border passing through the one or more first control points;
   displaying the IVUS image including the first modified border on the display device;
   wherein the steps of analyzing the IVUS image, determining the initial border and determining the first modified border are performed by one or more programmable processors;
   wherein the IVUS image is a single IVUS;
   dividing the IVUS image into a plurality of sectors;
   receiving a second user input indicating one or more second control points, wherein for each of the one or more second control points the second control point is located in one of the plurality of sectors either inside or outside of the modified border; and
   determining a second modified border based on the analysis, the first user input, and the second user input, wherein when at least one of the one or more first control points and at least one of the one or more second control points are both disposed the same sector of the plurality of sectors, the second modified border passes through the one or more second control points and ignores the one or more first control points.

2. The method of claim 1, wherein the analysis of the IVUS image includes an analysis of the brightness contrast between a plurality of pixels comprising the IVUS image.

3. The method of claim 1, wherein the initial border is a border of the luminal region of a blood vessel.

4. The method of claim 1, wherein the initial border is a medial-adventitial boundary of a blood vessel.

5. The method of claim 1, where analyzing the IVUS image comprises generating an edge strength map including 'a plurality of edge strength values corresponding to a plurality of pixels comprising the IVUS image.

6. The method of claim 5, where determining an initial border comprises performing an edge detection process to detect an edge based at least in part on the edge strength map, where the edge represents the initial border.

7. The method of claim 6, further comprising, generating a modified edge strength map based on the first user input selecting one or more control points;
   wherein determining the first modified border comprises performing the edge detection process to detect the edge based at least in part on the modified edge strength map, and wherein the edge represents the first modified border.

8. The method of claim 1, further comprising:
   receiving a third user input indicating one or more third control points; and
   determining a third modified border based on the analysis, the first user input, the second user input, and the third user input, wherein when at least one of the one or more third control points and at least one of either the one or more first control points or the one or more second control points are disposed in the same sector of the plurality of sector, the third modified border passes through the one or more third control points and ignores the one or more first control points and the one or more second control points.

9. The method of claim 1, wherein dividing the IVUS image into a plurality of sectors comprises dividing the IVUS image into a plurality of wedge-shaped sectors.

10. A method of analysis for an intravascular ultrasound (IVUS) image comprising:
   receiving the IVUS image;
   analyzing the IVUS image;
   determining an initial outer border of an outer region within the IVUS image based on the analysis of the IVUS image;
   determining an initial inner border of an inner region within the IVUS image based on the analysis of the IVUS image;
   receiving a first user input to modify one of the initial outer or initial inner borders;
   receiving a second user input interacting with a display device to indicate a first control point on the IVUS image displayed on the display device, where the first control point is independent of the initial border to be modified and located at a point other than on the initial border to be modified;
   when the first user input is to modify the initial outer border, then, determining a first modified outer border of the outer region is based on the analysis and the second user input, the first modified outer border passing through the first control point;
   when the first user input is to modify the initial inner border, then, determining a first modified inner border of the inner region is based on the analysis and the second user input, the first modified inner border passing through the first control point;
   displaying the IVUS image including the first modified border on the display device;
   wherein the steps of analyzing the IVUS image, determining the initial inner and outer borders and determining either the first modified inner border or the first modified outer border are performed by one or more programmable processors;
   wherein the IVUS image is a single IVUS image;
   dividing the IVUS image into a plurality of sectors;
   receiving a third user input to modify one of the initial outer border, the initial inner border, the first modified outer border, or the first modified inner border;
   receiving a fourth user input indicating a second control point, wherein the second control point is located in one of the plurality of sectors;
   when the fourth user input is to re-modify the first modified inner border, then, determining a second modified inner border is based on the analysis, the second user input, and the fourth user input;
   when the fourth user input is to re-modify the first modified outer border, then, determining a second modified outer border is based on the analysis, the second user input, and the fourth user input; and
   wherein when the first control point and the second control point are both disposed in the same sectors of the plurality of sectors, the second modified outer border passes through the second control point and ignores the first control point.

11. The method of claim 10 further comprising:
   receiving a fifth user input to modify one of the initial outer border, the initial inner border, the first modified outer border, the first modified inner border, the second modified outer border, or the second modified inner border;
   receiving a sixth user input indicating a third control point, wherein the third control point is located in one of the plurality of sectors;
   when the sixth user input is to re-modify the second modified inner border, then, determining a third modified inner border is based on the analysis, the second user input, the fourth user input, and the sixth user input;
   when the fourth user input is to re-modify the second modified outer border, then, determining a third modified outer border is based on the analysis, the second user input, the fourth user input, and the sixth user input; and
   wherein when the third control point and at least one of the first control point or the second control point are disposed in the same sector of the plurality of sectors, the third modified outer border passes through the third control point and ignores the at least one of the first control point or the second control point.

12. The method of claim 10, wherein dividing the IVUS image into a plurality of sectors comprises dividing the IVUS image into a plurality of wedge-shaped sectors.

13. A method of analysis for a medical image comprising:
   receiving a medical image;
   analyzing the medical image;
   determining an initial border of a region within the medical image based on the analysis of the medical image;
   receiving a first user input interacting with a display device to indicate one or more first control points on the medical image displayed on the display device, where each of the one or more first control points is independent of the initial border and located inside or outside of the initial border;
   determining a first modified border of the region based on the analysis and the first user input, the first modified border passing through the one or more first control points;
   displaying the medical image including the first modified border on the display device;
   wherein the steps of analyzing the medical image, determining an initial border and determining the first modified border are performed by one or more programmable processors;
   wherein the medical image is a single medical image;
   dividing the medical image into a plurality of sectors;
   receiving a second user input indicating one or more second control points, wherein for each of the one or more second control points the second control point is located in one of the plurality of sectors either inside or outside of the modified border; and determining a second modified border based on the analysis, the first user input, and the second user input, wherein when at least one of the one or more first control points and at least one of the one or more second control points are both disposed in the same sectors of the plurality of sectors, the second modified border passes through the one or more second control points and ignores the one or more first control points.

14. The method of claim 13, wherein the medical image is an echocardiograph image and the region represents a cardiac chamber.

15. The method of claim 13, wherein the medical image is an intravascular ultrasound (IVUS) image and the region represents a blood vessel.

16. The method of claim 15, wherein the initial border is a border of the luminal region of a blood vessel.

17. The method of claim 15, wherein the initial border is a medial-adventitial boundary of a blood vessel.

18. The method of claim 13, wherein the analysis of the medical image includes an analysis of the brightness contrast between a plurality of pixels comprising the medical image.

19. The method of claim 13, where analyzing the medical image comprises generating an edge strength map including a plurality of edge strength values corresponding to a plurality of pixels comprising the medical image.

20. The method of claim 19, where determining the initial border comprises performing an edge detection process to detect an edge based at least in part on the edge strength map, where the edge represents the initial border.

21. The method of claim 20, further comprising, generating a modified edge strength map based on the first user input selecting one or more first control points;
wherein determining the first modified border comprises performing the edge detection process to detect an edge based at least in part on the modified edge strength map, where the edge represents the first modified border.

22. A medical imaging system comprising:
a processor; and
a non-transitory computer-readable storage medium having processor-executable instructions, the processor-executable instructions when installed onto a system enable the system to perform actions, comprising:
receive a medical image;
analyze the medical image;
determine an initial border of a region within the medical image based on the analysis of the medical image;
receive a first user input interacting with a display device to indicate a first control point on the medical image displayed on the display device, where the first control point is independent of the initial border and located inside or outside of the initial border;
determine a first modified border of the region based on the analysis and the first user input, the modified border passing through the first control point;
wherein the medical image is a single medical image;
divide the medical image into a plurality of sectors;
receive a second user input indicating a second control point, wherein the second control point is located in one of the plurality of sectors either inside or outside of the modified border; and
determine a second modified border based on the analysis, the first user input, and the second user input, wherein when the first control point and the second control point are both disposed in the same sector of the plurality of sectors, the second modified border passes through the second control point and ignores the first control point.

23. The system of claim 22, wherein the medical image is an echocardiograph image and the region represents a cardiac chamber.

24. The system of claim 22, wherein the medical image is an intravascular ultrasound (IVUS) image and the region represents a blood vessel.

25. The system of claim 24, further comprising:
an ultrasound imaging device, the ultrasound imaging device being operable to generate the IVUS image.

26. The system of claim 22, further comprising:
a display device, the display device being operable to display the medical image; and
a user input device, the user input device being operable to interact with a user to receive the user input.

27. The system of claim 26, where the display device is further operable to display a graphical representation of the initial border superimposed on the display of the medical image.

28. The system of claim 26, where the display device is further operable to display a graphical representation of the first modified border superimposed on the display of the medical image.

29. The system of claim 22, wherein a plurality of first control points are received as the first user input.

30. The system of claim 22, wherein the analysis of the medical image is based on an analysis of the brightness contrast between a plurality of pixels comprising the medical image.

31. A method of analysis for a medical image comprising:
receiving the medical image;
analyzing the medical image;
determining an initial outer border of an outer region within the medical image based on the analysis of the medical image;
determining an initial inner border of an inner region within the medical image based on the analysis of the medical image;
receiving a first user input to modify one of the initial outer or initial inner borders;
receiving a second user input interacting with a display device to indicate a first control point on the medical image displayed on the display device, where the first control point is independent of the initial border to be modified and located at a point other than on the initial border to be modified;
when the first user input is to modify the initial outer border, then, determining a first modified outer border of the outer region based on the analysis and the second user input, the first modified outer border passing through the first control point;
when the first user input is to modify the initial inner border, then, determining a first modified inner border of the inner region based on the analysis and the second user input, the first modified inner border passing through the first control point;
displaying the medical image including the first modified outer border or the first modified inner border on the display device; and
wherein the steps of analyzing the medical image, determining the initial inner and outer borders and determining either the first modified outer border or the first modified inner border are performed by one or more programmable processors;
wherein the medical image is a single medical image;
dividing the medical image into a plurality of sectors;

receiving a third user input to modify one of the initial outer border, the initial inner border, the first modified outer border, or the first modified inner border;

receiving a fourth user input indicating a second control point, wherein the first modified inner border and is located in one of the plurality of sectors;

when the fourth user input is to re-modify the first modified inner border, then, determining a second modified inner border is based on the analysis, the second user input, and the fourth user input;

when the fourth user input is to re-modify the first modified outer border, then, determining a second modified outer border is based on the analysis, the second user input, and the fourth user input; and wherein when the first control point and the second control point are both disposed in the same sector of the plurality of sectors, the second modified outer border passes through the second control point and ignores the first control point.

32. The method of claim 31, wherein the medical image is an echocardiograph image and the region represents a cardiac chamber.

* * * * *